United States Patent [19]

Davis

[11] Patent Number: 5,312,890

[45] Date of Patent: * May 17, 1994

[54] POLYCARBONATE COMPOSITIONS COMPRISING BISPHOSPHINE OXIDE MONOMER

[75] Inventor: Gary C. Davis, Albany, N.Y.

[73] Assignee: General Electric Company, Schenectady, N.Y.

[*] Notice: The portion of the term of this patent subsequent to Mar. 16, 2010 has been disclaimed.

[21] Appl. No.: 51,145

[22] Filed: Apr. 22, 1993

[51] Int. Cl.$^5$ .............................................. C08G 64/08
[52] U.S. Cl. .................................. 528/167; 528/169; 528/196; 528/201; 528/204; 528/13; 528/14; 528/17
[58] Field of Search .............. 528/167, 169, 196, 201, 528/204

[56] References Cited

U.S. PATENT DOCUMENTS 5,003,029  3/1991  Ueda et al. ............................ 528/167
5,194,564  3/1993  Davis et al. .......................... 528/167

*Primary Examiner*—Harold D. Anderson
*Attorney, Agent, or Firm*—Edward A. Squillante; William H. Pittman

[57] ABSTRACT

Bisphosphine oxide monomers and homologs thereof may be incorporated into polycarbonates in order to obtain a flame retardant polymer. More particularly, bis[2,5-(diphenylphosphine oxide)]-1,4-hydroquinone and homologs thereof may be used to prepare flame retardant polycarbonates that retain high glass transition temperature and high impact resistances.

7 Claims, No Drawings

POLYCARBONATE COMPOSITIONS COMPRISING BISPHOSPHINE OXIDE MONOMER

FIELD OF THE INVENTION

This invention relates to new compositions of matter and more particularly to bisphosphine oxide monomers and polycarbonates derived therefrom. The resulting polycarbonates unexpectedly retain high glass transition temperatures, high impact resistances and flame retardancy.

BACKGROUND OF THE INVENTION

Polycarbonates are a well known class of high impact resistant thermoplastic resins characterized by optical clarity, high ductility as well as other advantageous properties. They are frequently employed as lenses and windows as a result of their transparency. Bisphenol A polycarbonate (BPA) is the predominant commercially available resin of this type. It is derived from 2,2-bis(4-hydroxyphenyl)propane, and ordinarily has a glass transition temperature of about 150° C.

It is of increasing interest to prepare polycarbonates which, while retaining the ductility of bisphenol A polycarbonates, have higher glass transition temperatures and are therefore more resistant to softening when heated. Moreover, there is need for polycarbonates which possess flame retardant properties since they are, for instance, conventionally used in the automotive and aircraft industries. Several flame retardant agents have been utilized in an attempt to produce flame retardant polycarbonates. For example, alkali metal salts of strong sulfonic acids are commonly used. However, when incorporated into the polycarbonate, the resulting polymer is hydrolytically sensitive. Further, when using these salts, it is also necessary to employ drip inhibitors or gas phase flame retardant agents. This is not ideal since drip inhibitors destroy the clarity of the polymer and gas phase retardants are often halogenated which creates problems with corrosion and toxicity. As an alternative to the above, phosphorus containing compounds such as triphenylphosphate have been used. When blended with a base polycarbonate, some flame retardant properties are observed. However, the resulting polymer blends are not desirable since they possess low glass transition temperatures (Tg) and low impact resistance when compared to the base resin.

The present invention is based on the discovery of bis[2,5-(diphenylphosphine oxide)]-1,4-hydroquinone and homologs thereof, and their incorporation into polycarbonates. The resulting bisphosphine oxide substituted polycarbonates are expected to exhibit improved flame retardancy since they possess phosphine oxide groups which increase polycarbonate limiting oxygen index values. Additionally, they are expected to retain high Tg values and impact resistances when compared to the base resin devoid of the bisphosphine oxide comonomer.

DESCRIPTION OF THE PRIOR ART

Accordingly, attempts have been made to prepare polycarbonates that possess high glass transition temperatures in addition to clarity and high ductility. In commonly assigned, copending applications, Ser. Nos. 07/989,309 and 07/989,310, it is disclosed that polycarbonates prepared from 1,3-bis(4-hydroxyphenyl)-1,3-dialkylcyclohexanes and bis[4'-4-(hydroxyphenyl)phenyl]alkanes, respectively, display glass transition temperatures on the order of about 10° C. to about 45° C. higher when compared to conventionally used polymers. Moreover, in commonly assigned, copending application Ser. No. 07/989,316, it is disclosed that polycarbonates prepared from heterocyclic bis(4-hydroxyphenyl)cycloalkanes possess glass transition temperatures on the order of about 35° C. to about 84° C. higher when compared to the typical resins. However, the polycarbonates of the present invention are distinguishable from the above polycarbonates since, among other reasons, the latter fail to consider flame retardancy by incorporation of phosphine oxide comonomers.

Other investigators have focused their attention on the flame retardancy of polycarbonates. As previously stated, attempts have been made to incorporate phosphorus containing additives in a flame retardant polymer formulation; however, the results have been unfavorable since glass transition temperatures and impact resistances have been adversely affected.

In commonly assigned U.S. Pat. No. 5,194,564, mono-phosphine oxide copolymers, which possess flame retardant properties as well as favorable Tg values, are disclosed. Nonetheless, the instant polycarbonates are distinguishable from the above mono-phosphine oxide copolymers since, among other reasons, they employ bisphosphine oxide comonomers in lieu of the well known mono-phosphine oxide comonomers mentioned above. The purpose is to achieve improved flame retardancy while maintaining base polymer stability.

Efforts to produce polycarbonates either ignore the important benefits which can be obtained by producing polycarbonates possessing high Tg values, polymer stability and flame retardancy or fail to simultaneously achieve them all.

SUMMARY OF THE INVENTION

The principal object of the present invention therefore is the discovery of a bisphosphine oxide monomer and a bisphosphine oxide substituted polycarbonate comprising the structural units of the formula

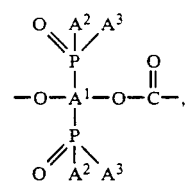

wherein $A^1$ is a tetravalent substituted or unsubstituted aromatic radical and $A^2$ and $A^3$ each are independently selected from aromatic radicals. Generally, 0.5–25 mole percent of the units of formula I are present in the bisphosphine oxide substituted polycarbonate, and preferably 2.5–10 mole percent of the total polymer consists of the units of formula I.

Additionally, the polycarbonates of the present invention can further comprise structural units of the formula

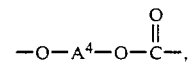

wherein $A^4$ is a divalent substituted or unsubstituted aromatic radical.

When employing the mono-phosphine oxide comonomer discussed in U.S. Pat. No. 5,194,564, greater amounts of the comonomer are required to produce the desired copolymer displaying favorable flame retardancy. This can cause a decrease in base polymer stability.

Characteristically, phosphorus monomers used to prepare polyesters and polycarbonates cause hydrolytically unstable phosphorus oxygen bonds to form which leads to inferior base polymer properties as well as molecular weight degradation. These unstable phosphorus oxygen bonds are less prevalent when utilizing a bisphosphine oxide. When producing the desired conventional phosphine oxide substituted polycarbonate, a greater mole percent of the mono-phosphine comonomer is required when compared to the bisphosphine oxide comonomer of the instant invention. This is true because the former possesses a much lower weight percent of phosphorus in comparison to its bisphosphine oxide counterpart. Thus, in order to obtain the Tg values and flame retardancy of the polycarbonates of the instant invention, greater amounts of the mono-phosphine oxide comonomer would have to be incorporated into the base polymer chain resulting in poor base polymer stabilities and molecular weight degradation.

The additional features and advantages of the invention will be made evident upon reference to the following detailed description.

DETAILED DESCRIPTION OF THE PREFERRED EMBODIMENTS

Polycarbonates are generally formed by the reaction of a dihydroxyaromatic compound and a carbonate source.

One reactant for formation of the polycarbonates of this invention is a dihydroxyaryldiphosphine oxide (bisphosphine oxide monomer) of the formula

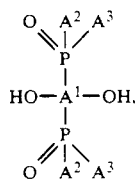

III wherein $A^1$, $A^2$ and $A^3$ are as previously described. Specifically, $A^1$ can be

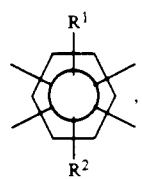

IV wherein $R^1$ and $R^2$ are hydrogen, halogens, alkyl or aryl radicals and preferably para to each other. $A^2$ and $A^3$ may be any unsubstituted aromatic radical or substituted derivatives thereof. Suitable substituents include alkyl, alkenyl, halo, nitro, alkoxy and the like. Unsubstituted phenyl radicals are preferred. The hydroxy groups of formula III are preferably para to each other.

Bis[2,5-(diphenylphosphine oxide)]-1,4-hydroquinone may be prepared by the reaction of a quinone and a phosphine oxide or a suitably treated chlorophosphine. The formation of the instant bisphosphine oxide monomer was discovered during the synthesis of a dihydroxyarylphosphine oxide via a process similar to the one mentioned in U.S. Pat. No. 5,003,029. Illustrative quinones include parabenzoquinone, 1,4-naphthoquinone, 1,4-anthraquinone, methyl-p-benzoquinone and dimethyl-p-benzoquinone. The preferred quinone is p-benzoquinone. Suitable phosphine oxides or chlorophosphine include diphenyl phosphine oxide or diphenyl chlorophosphine.

Additionally, the synthesis of mono-phosphine oxide monomers is described in Zh Obshch. Khim, 1972, 42 (11), 2415-18, Chem Comm., 1966 (15), 505-6 and USSR patents 302 and 346.

The preferred bisphosphine oxide monomer of the instant invention is bis[2,5-(diphenylphosphine oxide)]-1,4-hydroquinone and can be prepared as disclosed by the examples which follow.

EXAMPLE 1

Into a 50 cc single-neck round bottom flask equipped with a magnetic stir bar reflux condenser and $N_2$ bypass was placed 0.5 g (55 mmols) of p-benzoquinone along with 1.0 g (5 mmols) of diphenyl phosphine oxide and 10 mL of 2-ethoxyethanol. The reaction mixture was stirred at 125° C. and after about 15 minutes a precipitate began to form. After 2 hours, the reaction mixture was cooled and filtered. The yellow product obtained was washed with a small amount of 2-ethoxyethanol and dried. The product weighed 0.67 g and melted at 253°-254° C. An $H^1$NMR ($d^6$-DMSO) analysis showed that a 50/50 mixture of 2,5-dihydroxyphenyldiphenylphosphine oxide and bis[2,5-(diphenylphosphine oxide)]-1,4-hydroquinone was formed. The latter bisphenol was concentrated to one-third volume by treating with acetone. The concentrated product was then recrystallized from ethanol/water to produce the desired product. The structure was confirmed by $^1H$ and $^{13}C$ NMR ($d^6$-DMSO) testing.

EXAMPLE 2

Into a 100 cc single-neck round bottom flask equipped with a magnetic stir bar was placed 4.5 g (14.5 mmols) of 2,5-dihydroxyphenyldiphenylphosphine oxide along with 6.0 g of sodium sulfate, 3.6 g (15.5 moles) of silver oxide and 60 mL of acetone. The reaction mixture was stirred at room temperature for 17 hours, followed by filtration and removal of the acetone to give 4.5 g of a brown sticky solid. $^1H$ NMR ($CDCl_3$) study showed that 2-diphenylphosphine oxide-1,4-benzoquinone was formed. To 1.54 g (5 mmols) of the benzoquinone above, in raw form, was added 1.0 g (5 mmols) of diphenylphosphine oxide dissolved in 20 mL of toluene. After stirring for about 5 minutes at room temperature, a tan precipitate was formed. Stirring was continued for 1.5 hours at which time the product was filtered and washed with toluene and dried to produce 2.12 g of bis[2,5-(diphenylphosphine oxide)]-1,4-hydroquinone which was shown to be pure by $^1H$ NMR study.

Homologs of the bisphosphine oxide monomers prepared above may be prepared from additional precursor quinones. They too would make suitable comonomers for flame retardant polycarbonates and polyesters thereof.

Moreover, the above bisphosphine oxide monomers and homologs thereof would be useful for flame retardant strategy and stabilization in polymer systems other than polyesters and polycarbonates.

The phosphine oxide containing polycarbonates above may be formed by any method conventional in the art. Examples of methods to prepare phosphine oxide containing polycarbonates include an interfacial process, a transesterification process and a bishaloformate process.

The preferred method of forming the phosphine oxide substituted polycarbonates is interfacially, that is, in a mixed aqueous-organic system which results in recovery of the polycarbonate in the organic phase. A carbonate precursor is used in the interfacial reaction and is preferably phosgene. When using an interfacial process it is also standard practice to use a catalyst system well known in the synthesis of polycarbonates and copolyestercarbonates. Suitable catalysts include tertiary amines. Tertiary amines include aliphatic amines such as triethylamine, tri-n-propylamine, diethyl-n-propylamine, and tri-n-butylamine, and highly nucleophilic heterocyclic amines such as 4-dimethylaminopyridine. Such amines generally contain at least about 6 and preferably about 6-14 carbon atoms. The most useful amines are trialkylamines containing no branching on the carbon atoms in the 1- and 2-positions. Triethylamine is the most preferred.

A chain terminating agent to control the molecular weight of the polymers is usually present. Suitable chain termination agents are those commonly employed for polycarbonate formation, including monohydroxyaromatic compounds such as phenol, p-t-butylphenyl and p-cumylphenol. Phenol is preferred. Quantities of chain terminating agents can range from about 0.5 to about 7 mole percent based on the total amount of non-phosphorus dihydroxyaromatic compound employed.

Another method of preparing polycarbonates is by transesterification with a bisphenol of a carbonate ester such as diphenyl carbonate or a bis-polyfluoroalkyl carbonate. U.S. Pat. Nos. 4,217,438, 4,310,656 and 4,330,664 describe the formation of polycarbonates by a transesterification method and are hereby incorporated by reference.

Still another method of polycarbonate formation is the reaction of bishaloformates with alkali metal hydroxides and various amines. One method for reaction bishaloformates with dihydroxy compounds is disclosed in U.S. Pat. 4,737,573 which is hereby incorporated by reference. Generally bischloroformate oligomer compositions are prepared by passing phosgene into a heterogeneous aqueous-organic mixture containing at least one dihydroxyaromatic compound. The reaction is a condensation reaction that typically takes place interfacially.

The polycarbonates of the present invention can include both homo- and copolycarbonates. The copolycarbonates preferably contain about 0.5 mole percent to about 25 mole percent dihydroxyarylbisphosphine oxide units and more preferably contain about 2.5 mole percent to about 10 mole percent units.

The non-phosphorus dihydroxyaromatic compounds useful for forming copolycarbonates may be any such compound known to the art. The material represented by the formula

HO-A⁴-OH     V is the source of the structural units of formula II above. Illustrative non-limiting examples of non-phosphorus dihydroxyaromatic compounds include:
2,2-bis(4-hydroxyphenyl-propane (bisphenol A);
2,2-bis(3,5-dibromo-4-hydroxyphenyl)propane;
2,2-bis(3,5-dimethyl-4-hydroxyphenyl)propane;
1,1-bis(4-hydroxyphenyl)cyclohexane;
1,1-bis(3,5-dimethyl-4-hydroxyphenyl)cyclohexane;
1,1-bis(4-hydroxyphenyl)decane;
1,4-bis(4-hydroxyphenyl)propane;
1,1-bis(4-hydroxyphenyl)cyclododecane;
1,1-bis(3,5-dimethyl-4-hydroxyphenyl)cyclododecane;
4,4-dihydroxydiphenyl ether;
4,4-thiodiphenol;
4,4-dihydroxy-3,3-dichlorodiphenyl ether; and
4,4-dihydroxy-3,3-dihydroxydiphenyl ether.

Other useful non-phosphorus dihydroxyaromatic compounds which are also suitable for use in the preparation of the above polycarbonates are disclosed in U.S. Pat. Nos. 2,999,835; 3,028,365; 3,334,154 and 4,131,575, all of which are incorporated herein by reference. The preferred bisphenol is 2,2-bis(4-hydroxyphenyl)propane (bisphenol A).

The following example depicts the formation of the bisphosphine oxide substituted copolycarbonate of the instant invention.

EXAMPLE 3

The phosphine oxide containing copolycarbonate was prepared by interfacial phosgenation of a mixture of 21.7 g of BPA, 2.55 g of 2,5-(diphenylphosphine oxide)-1,4-hydroquinone (5 mole % compared to BPA), 0.32 g of p-cumylphenol chainstopper and 0.2 g of triethylamine in 125 mL of methylene chloride and 100 mL of water. To the vigorously stirred emulsion was added 15.2 g of phosgene over a 0.5 hour period. Once the reaction was complete, the phases were separated and the polymer solution (methylene chloride layer) was washed two times with 300 mL of 0.1N HCL followed by five times with 300 mL of distilled water. The polymer solution was precipitated into 1 L of methanol in a blender. The white powder obtained was isolated and dried at 120° C. GPC analysis of the polymer shows an Mn=15,000. ¹H and ³¹P NMR analysis confirmed the incorporation of 2,5-(diphenylphosphine oxide)-1,4-hydroquinone into the polymer. The copolymer gave a strong, clear, colorless solvent cast film and the Tg of the copolymer determined by DSC is 150° C.

What is claimed is:

1. A polycarbonate polymer comprising the structural units of the formula

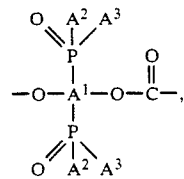

wherein $A^1$ is a tetravalent or hexavalent substituted or unsubstituted aromatic radical and $A^2$ and $A^3$ each are independently selected from aromatic radicals.

2. A polycarbonate polymer in accordance with claim 1 wherein $A^1$ is defined by the formula

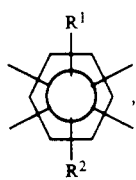

and $R^1$ and $R^2$ are hydrogen, halogens or alkyl or aryl radicals.

3. A polycarbonate polymer in accordance with claim 1 wherein $A^1$ is defined by the formula

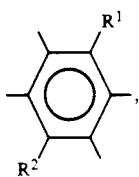

and $R^1$ and $R^2$ are hydrogen, halogens, alkyl or aryl radicals and para to each other.

4. A polycarbonate polymer in accordance with claim 1 wherein each of $A^2$ and $A^3$ is a phenyl radical.

5. A polycarbonate polymer in accordance with claim 1 wherein 0.5–25 mole percent of the structural units of the formula

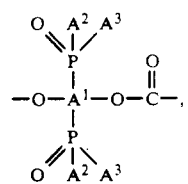

are present in the polymer.

6. A polycarbonate polymer in accordance with claim 1 wherein 2.5–10 mole percent of the structural units of the formula

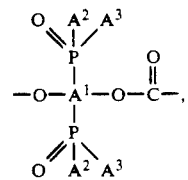

are present in the polymer.

7. A polycarbonate polymer in accordance with claim 1 further comprising the structural units of the formula

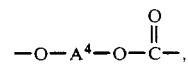

wherein $A^4$ is a divalent aromatic radical.

* * * * *